United States Patent
Heppe et al.

(10) Patent No.: US 9,968,298 B2
(45) Date of Patent: May 15, 2018

(54) METHOD AND DEVICE FOR FOLDING A COVER ON A MEDICAL SENSOR

(71) Applicant: FRESENIUS MEDICAL CARE DEUTSCHLAND GMBH, Bad Homburg (DE)

(72) Inventors: John Heppe, St. Wendel (DE); Roland Rullof, Lebach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 372 days.

(21) Appl. No.: 14/778,519

(22) PCT Filed: Mar. 17, 2014

(86) PCT No.: PCT/EP2014/055346
§ 371 (c)(1),
(2) Date: Sep. 18, 2015

(87) PCT Pub. No.: WO2014/147040
PCT Pub. Date: Sep. 25, 2014

(65) Prior Publication Data
US 2016/0287176 A1    Oct. 6, 2016

(30) Foreign Application Priority Data
Mar. 19, 2013   (DE) .......................... 10 2013 004 672

(51) Int. Cl.
A61B 19/08    (2006.01)
A61B 5/00     (2006.01)
(Continued)

(52) U.S. Cl.
CPC .......... *A61B 5/6833* (2013.01); *A61M 1/3656* (2014.02); *A61B 2562/12* (2013.01); *A61M 2005/1588* (2013.01); *A61M 2207/00* (2013.01)

(58) Field of Classification Search
CPC ... A61B 5/6833; A61B 2562/12; A61B 19/08; A61B 2019/085; A61B 19/12;
(Continued)

(56) References Cited

U.S. PATENT DOCUMENTS 4,415,325 A    11/1983 Fuchs et al.
5,162,040 A    11/1992 Annett
(Continued)

FOREIGN PATENT DOCUMENTS

CN    101224643 A    7/2008
CN    102811753 A    12/2012
(Continued)

OTHER PUBLICATIONS

International Search Report in PCT/EP2014/055346, dated Jun. 10, 2014 (English).
(Continued)

*Primary Examiner* — Ophelia A Hawthorne
(74) *Attorney, Agent, or Firm* — Kilyk & Bowersox, P.L.L.C.

(57) ABSTRACT

A method and a device for folding a cover material on a medical sensor having a carrier material which is to be fixed to the skin of a patient and which, on the side facing the patient, is provided with an adhesion or adhesive layer to which the cover material is applied, wherein a section of the cover material which is opposite an adhesion-layer-free section of the carrier material forms a tab. The method and the device are based on the use of a tool for folding the cover material which has at least two contact surfaces which intersect at an edge which runs parallel to the plane of the combination of carrier material and cover material. The tool is moved on an axis which runs at an angle to the plane of the combination of carrier material and cover material in such a way that the tab is gripped by the tool and folded over by the tool. After the tab has been folded over, pressure is applied to the folded-over section of the carrier material to produce a folded edge.

28 Claims, 6 Drawing Sheets

(51) Int. Cl.
 *A61M 1/36* (2006.01)
 *A61M 5/158* (2006.01)
(58) Field of Classification Search
 CPC .... A61B 19/10; A61B 19/087; A61M 1/3656; A61M 2005/1588; A61M 2207/00
 See application file for complete search history.

(56) References Cited

U.S. PATENT DOCUMENTS

| | | |
|---|---|---|
| 5,840,052 A | 11/1998 | Johns |
| 7,708,679 B2 | 5/2010 | Cailloux et al. |
| 2015/0328389 A1 | 11/2015 | Heppe |

FOREIGN PATENT DOCUMENTS

| | | |
|---|---|---|
| DE | 3935003 A1 | 4/1991 |
| EP | 2325122 A1 | 5/2011 |
| GB | 2297260 A | 7/1996 |
| WO | 2004060674 A1 | 7/2004 |
| WO | 2008032623 A1 | 3/2008 |
| WO | 2011116943 A1 | 9/2011 |

OTHER PUBLICATIONS

International Preliminary Report on Patentability in PCT/EP2014/055346, dated Sep. 22, 2015.
Search Report, For Chinese Patent Application No. 201480016476.2, issued by the Chinese State Intellectual Property Office (SIPO), 2 pages.

METHOD AND DEVICE FOR FOLDING A COVER ON A MEDICAL SENSOR

CROSS REFERENCE TO RELATED APPLICATIONS

The present application is the national stage entry of International Patent Application No. PCT/EP2014/055346, filed on Mar. 17, 2014, and claims priority to Application No. DE 10 2013 004 672.6, filed in the Federal Republic of Germany on Mar. 19, 2013, the disclosures of which are expressly incorporated herein in its entirety by reference thereto.

FIELD OF INVENTION

The present invention relates to a method and a device for folding a cover material on a medical sensor having a carrier material which, in particular, is to be fixed to the skin of a patient and which, on the side facing the patient, is provided with an adhesion layer to which the cover material is applied, wherein a section of the cover material which is opposite an adhesion-layer-free section of the carrier material forms a tab.

BACKGROUND

Various devices, with which fluids can be taken from patients or fluids can be fed to the patient by means of a flexible tube, are known in the field of medical engineering. Here, access to the patient generally takes place with a catheter for feeding into bodily organs or a cannula for puncturing vessels. Orderly access to the patient must be ensured during the examination or treatment. It is therefore necessary to monitor the patient access. In particular, orderly patient access requires extracorporeal blood treatment devices which have an extracorporeal blood circuit.

Devices, which have an electrical moisture sensor in order to be able to detect blood escaping at the puncture point, are known for monitoring vessel access in the case of extracorporeal blood treatment devices. The known moisture sensors are in the form of a pad which is placed on the puncture point.

A woven moisture sensor, which has a connecting tab on which the electrical connecting contacts are arranged, is disclosed in International Patent Publication No. WO 2011/116943 A1. The sensor has a textile fabric which is placed on the patient's skin. The textile fabric of the sensor is provided with an adhesive or adhesion layer which is covered by a removable cover material. The adhesive or adhesion layer is designed in such a way that the sensor can be fixed to the patient's skin after the cover material has been removed.

It should be possible to produce medical sensors cost-effectively in large quantities. For easy handling of medical sensors, the cover material should be easy to remove from the carrier material.

SUMMARY

The present invention is based on the object of providing a method with which the large-quantity production of medical sensors, which are easy to handle, is simplified. In addition, an object of the present invention is to create a device with which the large-quantity production of easy-to-handle medical sensors is simplified. In particular, the present invention is based on the object of providing a method and a device for folding a cover material on a medical sensor.

The method according to the present invention and the device according to the present invention allow the production of medical sensors, with which a section of the cover material forms a protruding tab which is easy to grip.

The tab is created in that the carrier material has an adhesion or adhesive layer on one side in a first section and no adhesion or adhesive layer in a second section so that the cover material in the second section which is free from the adhesion or adhesive layer is not stuck to the carrier material. The method according to the present invention and the device according to the present invention provide that the tab is folded over and provided with a folded edge.

After the cover material has been folded, the tab which protrudes from the carrier material can be easily gripped even with protective gloves. This is of advantage, particularly, in the case of medical sensors which have to be handled with protective gloves under sterile conditions, in particular, in the case of moisture sensors for monitoring vessel access.

In the following, an adhesion or adhesive layer is understood to mean any layer which, on the one hand, creates an adequate bond between carrier and cover material and, on the other, allows the cover material to be removed from the carrier material. In addition, it must be possible to produce an adequately adhesive bond between the carrier material and the patient's skin with the adhesion or adhesive layer.

The production method allows the cover material to be applied over the whole area of the carrier material without the need for overlapping sections to enable the tab to be gripped more easily. As the tab does not project, the sensor can be more easily cut or stamped out from the combination of carrier material and cover material than when overlapping regions are provided, as a result of which the production costs of the sensors are reduced. Only one cutting or stamping operation is required to separate the sensors from a material web.

The method according to the present invention and the device according to the present invention are based on the use of a tool for folding the cover material which has at least two contact surfaces which intersect at an edge which runs parallel to the plane of the combination of carrier material and cover material. The tool is moved on an axis which runs at an angle to the plane of the combination of carrier material and cover material in such a way that the tab is gripped by the tool and folded over by the tool. When the tool is moved towards the tab, the first contact surface of the tool faces towards the tab and the second contact surface faces away from the tab. When the tool is fed forwards, the tab is gripped by the first contact surface. After folding over, the folded-over tab is held by the second contact surface. To produce a folded edge, pressure is applied to the folded section of the carrier material so that the tab remains in the folded-over position even after the tool is removed.

In practice, it has been shown that, when the cover material is laminated by machine, the carrier material which is free from the adhesion or adhesive layer and the tab can also stick together in the section of the carrier material which is free from the adhesion or adhesive layer due to adhesion forces. In this case, the tab cannot be reliably gripped by the tool. A preferred exemplary embodiment therefore provides that the section of the carrier material which is free from the adhesion or adhesive layer is separated from the tab before the tool is used.

When the tab has been reliably gripped and folded over, the positioning of the tool and the alignment of the contact surfaces can be changed. An optimum positioning and alignment is achieved, however, when the first contact surface runs substantially orthogonally with respect to the axis on which the tool is moved, and the second contact surface lies in a plane which runs substantially parallel to the plane of the combination of carrier material and cover material. This ensures that the tab is reliably gripped and uniformly folded over while the tool is being fed forwards.

For the production of a defined folded edge, the carrier material must be adequately supported when pressure is applied to the folded section of the cover material. A preferred exemplary embodiment therefore provides a third contact surface on the tool which lies opposite the second contact surface. When pressure is applied to the folded section of the cover material, the folded section of the cover material is pressed against the third contact surface. The second and third contact surface are optimally aligned with one another when they run substantially parallel to one another.

The third contact surface is preferably provided on the preferably single-piece tool. However, it is also possible that the contact surface for supporting the carrier material is formed from one part which is not an integral part of the tool.

The length of the second contact surface should be calculated so that the folded-over tab is gripped over substantially its whole length on the side opposite the carrier material, while the length of the third contact surface should be calculated so that only the section of the folded-over cover material in the region of the fold is gripped. The third contact surface therefore springs back with respect to the first contact surface. The length of the second contact surface should therefore correspond approximately to the length of the folded-over tab, and the length of the third contact surface approximately to the length of the section of the folded-over cover material in the region of the fold.

In a further preferred exemplary embodiment, the second and third contact surface form the lateral boundaries of a groove in the tool such that the base of the groove forms a stop for the folded-over section of the cover material in order to be able to bring the folded-over tab exactly into the position in which the folded edge is intended to lie. Advantageously, the exact positioning takes place in that the folded-over section of the cover material is pressed against the base of the groove before the folded-over section is pressed against the third contact surface.

For exact positioning, a preferred exemplary embodiment provides a positioning element which is pushed forward into the groove in a plane parallel to the plane of the combination of carrier material and cover material so that the folded-over section of the cover material is pressed against the base of the groove.

In a further preferred exemplary embodiment, to compensate for component tolerances, the folded-over section of the cover material is retracted once more by a predetermined distance before the folded-over section of the cover material is pressed against the third contact surface. This ensures that pressure is exerted on the folded-over section in an exactly defined region.

The combination of carrier material and cover material is preferably laid on a contact surface in such a way that the tab extends beyond the contact surface so that the tab is freely accessible to the tool.

A gripper element, which grips the side of the carrier material facing away from the cover material, is preferably provided in order to separate the section of the carrier material which is free from the adhesion or adhesive layer from the tab. In order to lift the carrier material off the tab, the gripper element is swiveled about an axis which runs parallel to the plane of the combination of carrier material and cover material. In practice, it can be of advantage to grip and fold over the section concerned of the carrier material with the gripper element several times. During the swiveling movement of the gripper element, the tab is held on the side facing away from the carrier material, preferably by a holding element.

The device according to the present invention for folding a cover material has a holding device, which has a contact surface on which to place the sensor, and the tool according to the present invention as well as a contact-pressure element for producing the folded edge.

The individual components of the device according to the present invention can be moved with the known linear guides. The components can be driven by means of the known drive units, for example, by means of pneumatic, hydraulic, and/or electrical drives. The individual components of the device according to the present invention for carrying out the individual steps of the method according to the present invention can be actuated fully automatically by a control unit. The device according to the present invention can also have an automatic feed device for depositing and removing the sensors (pads) which is controlled fully automatically by the control unit.

An exemplary embodiment of the present invention is explained in more detail below with reference to the accompanying drawings.

DETAILED DESCRIPTION

Figure 1:
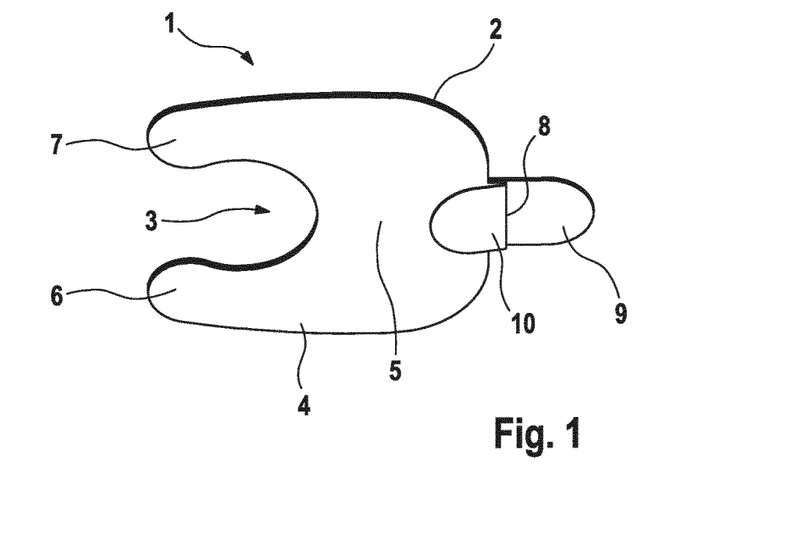
FIG. 1 shows an exemplary embodiment of a medical sensor.

FIG. 1 shows an exemplary embodiment of a medical sensor 1. In this exemplary embodiment, the medical sensor is an electrical moisture sensor which can be placed on the patient's skin at the puncture point. The moisture sensor is a pad which has a textile fabric 2 (gauze) which is made of conducting and non-conducting warp and weft threads. The conducting warp and weft threads form an electrically conducting structure in the gauze 2 for measuring moisture. On the side facing the patient when the sensor is in use, the sensor 1 has an adhesive or adhesion layer which is covered by a removable cover material 4.

The medical sensor 1 has a central region 5 with two legs 6, 7 which encompass the sides of a semicircular section 3. A connecting tab 9, which lies opposite the two legs, is connected to the central region 5. The connecting contacts for the electrically conducting structure, which are not shown in FIG. 1, are located on the connecting tab 9. The cover material 4 is folded over and provided with a folded edge 8 in the region of the connecting tab 9. The folded-over section of the cover material 4 therefore forms a removal tab 10.

Figure 2:
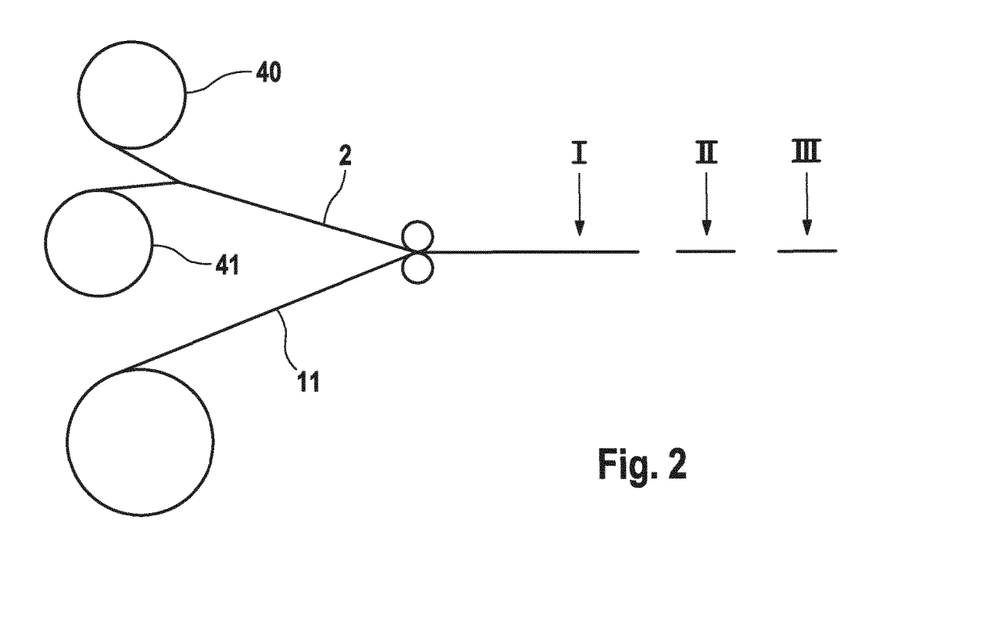
FIG. 2 shows the main method steps for producing the moisture sensor in a highly simplified schematic diagram.

FIG. 2 shows the main method steps for producing the sensor. The warp threads and the weft threads 40, 41 are fed in to produce the gauze web 2. A layer 11, with which the gauze web 2 is laminated, is fed in during the web process. After the gauze 2 has been produced, further method steps known to the person skilled in the art, which include, for example, finishing, in particular, washing, fixing or heat treatment, are carried out. In a further method step I, the individual sensors are separated. The sensors are checked in a further method step II. Finally, the sensors are assembled in a further method step III.

The layer 11 which is to be laminated with the gauze web 2 is a foil or barrier layer, which is adhesive or sticky on both sides in certain areas and is covered on one side by a cover material 4 (liner). The two adhesive or adhesion layers of the foil can have different properties. The adhesive or adhesion layer on the one side is intended to bond the gauze web 2 and the foil of the layer 11 securely to one another, while the adhesive or adhesion layer on the other side serves only to retain the removable cover material 4 and to provide the adhesion of the sensor to the patient's skin. The cover material 4 serves to protect the sensor 1 and is removed and thrown away before the sensor is applied to the patient's skin (FIG. 1).

On the side facing the cover material, the foil of the layer 11 has strip-shaped regions which run in the longitudinal direction (production direction) and are free from the adhesive or adhesion layer, so that the cover material 4 does not stick to the foil in these regions and forms tabs when the sensors are separated (FIG. 1).

Figure 3:
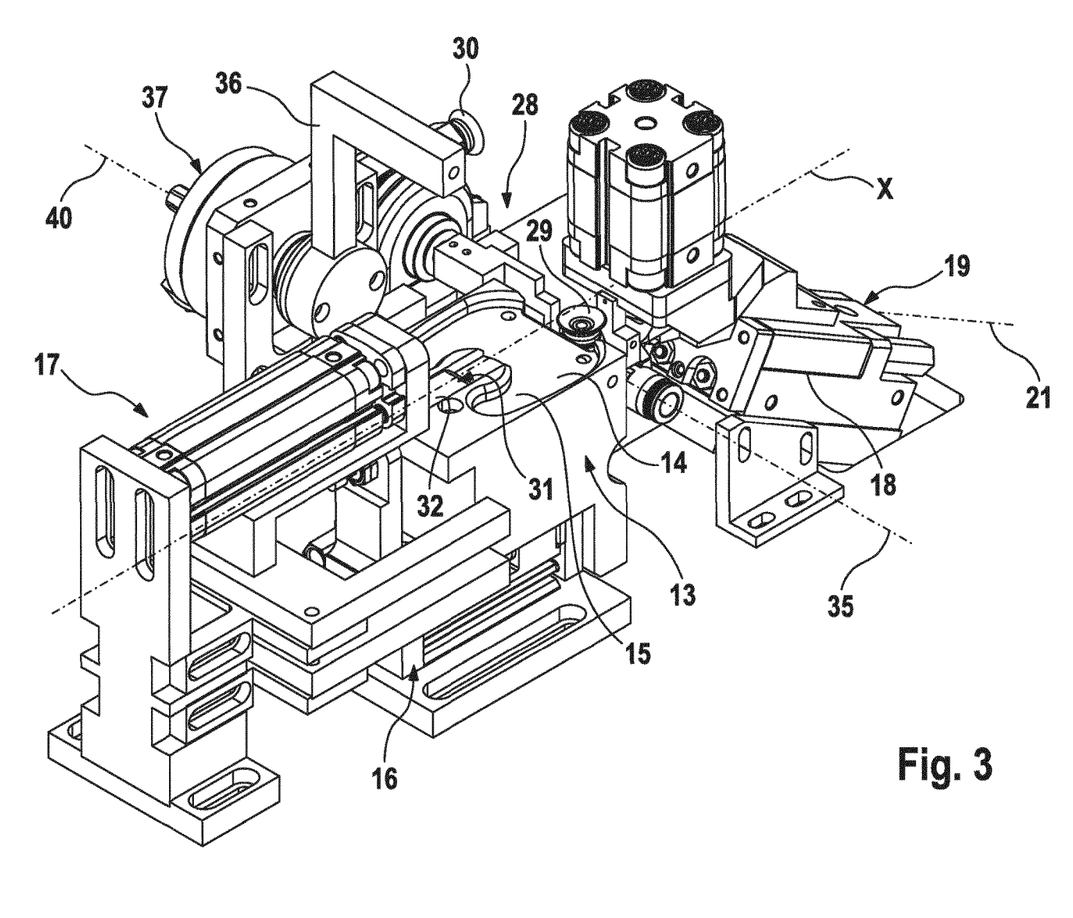
FIG. 3 shows the device according to the present invention in perspective view.
Figure 5A:
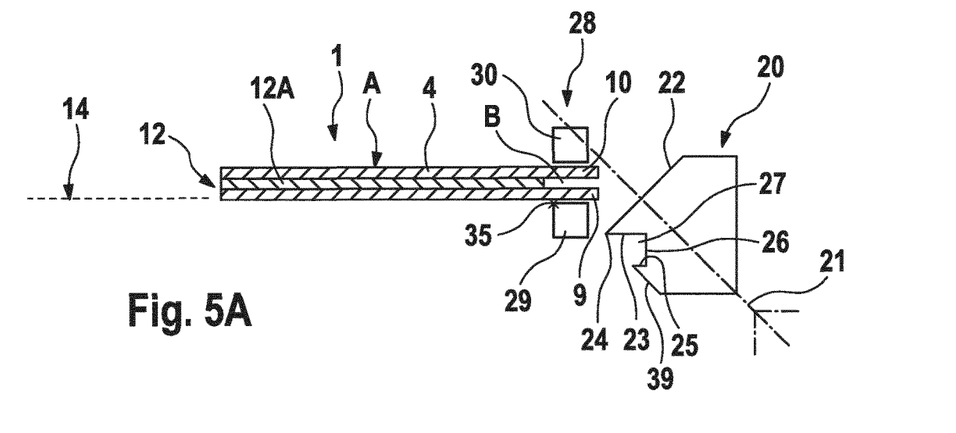
FIG. 5A shows the folding tool and the holding and gripper element of the device according to the present invention in a highly simplified schematic diagram, in which the tool is in the starting position.

FIG. 5A shows a section through the separated sensor 1 which is placed in the device according to the present invention, which is shown only in highly simplified schematic form. The gauze web 2 and the foil or barrier layer of the layer 11 are hereinafter referred to as carrier material 12 of the sensor 1. In FIG. 3, the carrier material 12 is shown as a cohesive layer, as it is immaterial for the present invention whether the carrier layer consists of a plurality of layers or thicknesses. It is only of significance for the present invention that the carrier layer is free from the adhesive or adhesion layer in one region in order to form the tab.

The carrier material 12 has a first section A which is provided with the adhesion or adhesive layer 12A, and a second section B in which the carrier material 12 is not provided with an adhesion or adhesive layer. In the present exemplary embodiment, the section B of the carrier material 12 which is free from the adhesion or adhesive layer is the connecting tab 9. As the cover material 4 does not stick to the carrier material 12 in the section which is free from the adhesion or adhesive layer, the cover material 4 in this section forms the removal tab 10. In order to be able to easily grip the removal tab 10, the cover material 4 is folded so that the tab protrudes from the carrier material. As the sensor 1 does not stick to the patient's skin in the region of the tab due to the absence of the adhesion or adhesive layer at this point, the sensor can be easily connected to an electrical connecting terminal and, after use, easily gripped by the tab and removed from the skin.

For the production of the sensors 1 in large quantities, an aim is that the cover material 4 can be easily folded after the sensors have been separated. In doing so, a clean folded edge 8 may be created at a defined position.

The device according to the present invention for folding the cover material 4 is described in detail below with reference to FIGS. 3 and 4 and 5A to 5H.

Figure 4:
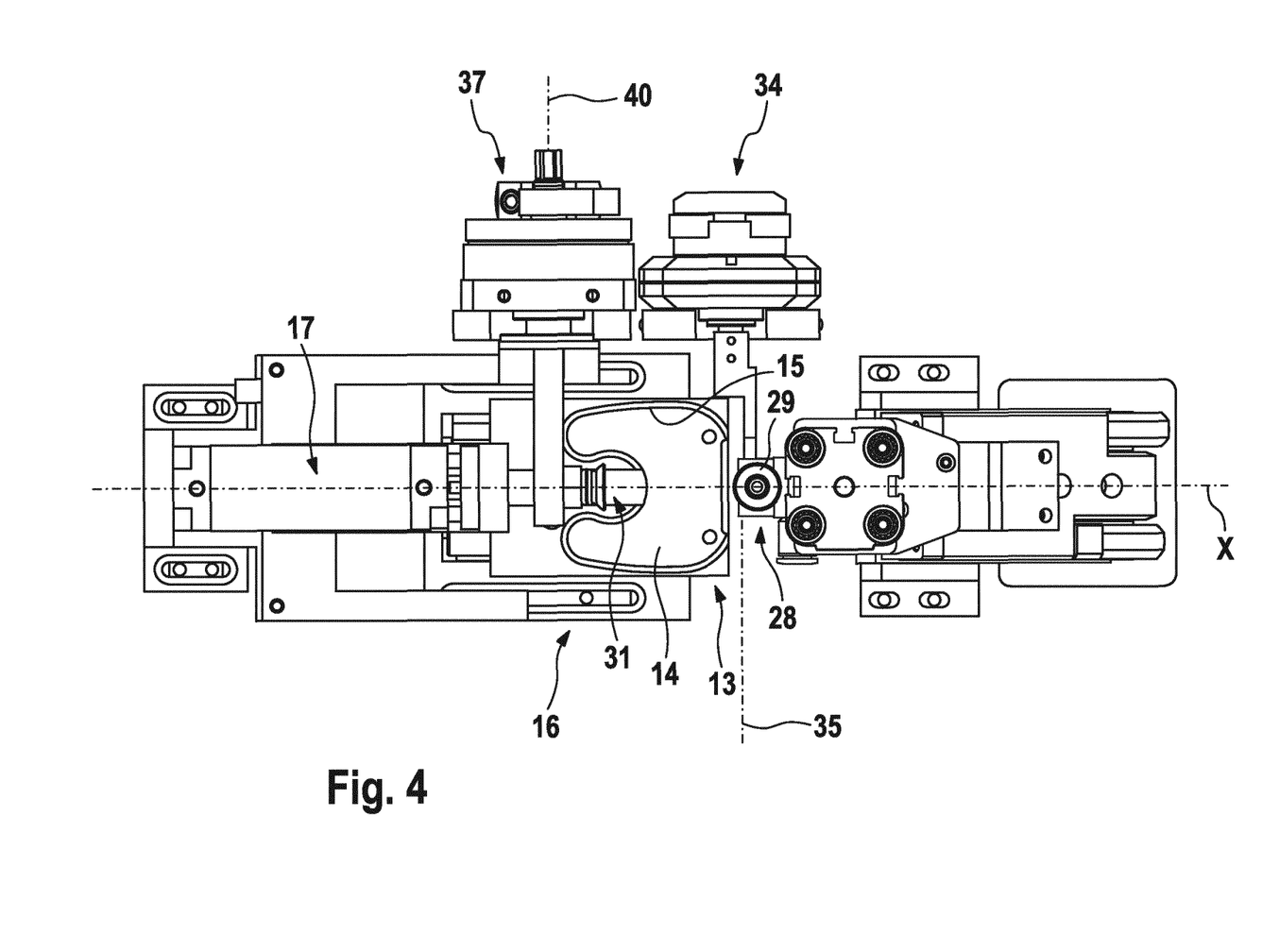
FIG. 4 shows the device according to the present invention in plan view.

FIGS. 3 and 4 show the main components of the device according to the present invention, while the individual method steps with which the cover material 4 is folded over and the folded edge 8 is produced are shown in FIGS. 5A to 5H. In the figures, the same references are used for corresponding parts.

The device according to the present invention has a holding device 13 for fixing the sensor 1. The holding device 13 has a contact surface 14 with a contoured depression 15. The depression 15 is formed in such a way that the central region 5 and the two legs 6, 7 of the sensor 1 can be fitted therein. The depression 15 extends as far as the edge of the contact surface 14 so that the connecting and removal tabs 9, 10 of the sensor extend forward beyond the contact surface 14. The central longitudinal axis of the device, which runs through the sensor resting on the contact surface 14, is designated by the reference X.

The holding device 13 is movably guided by means of a linear guide on the longitudinal axis X of the device over a predetermined distance between a front and a back position. In the present exemplary embodiment, the longitudinally movable guided holding device 13 is driven by a pneumatic drive device. Linear guide and drive device form a unit 16 which is arranged below the holding device 13. This unit 16 can be a pneumatic cylinder with linear guide which is also referred to as a mini slide.

In front of the holding device 13 are a linear guide and drive device for a folding tool which cannot be seen in FIGS. 3 and 4. Linear guide and drive device again form a unit which is designated by the reference 18. The tool can be moved along an axis 21 which runs at an angle to the contact surface 14. The angle between the axis 21 and the contact surface 14 preferably lies between 30° and 60°, in particular, 45°.

FIGS. 5A to 5H show the sensor 1 and the tool 20 of the device according to the present invention in a highly simplified diagram, in which the sensor 1 rests on the contact surface 14 of the holding device (not shown). The front section of the carrier material 12 forms the connecting tab 9 with the electrical connecting contacts, and the front section of the cover material 4, which does not stick to the carrier material, forms the removal tab 10.

In FIGS. 5A to 5H, the forward feed of the folding tool 20 on the axis 21 which runs at an angle to the surface of the sensor is shown in individual steps from the starting position to the end position.

Figure 5B:
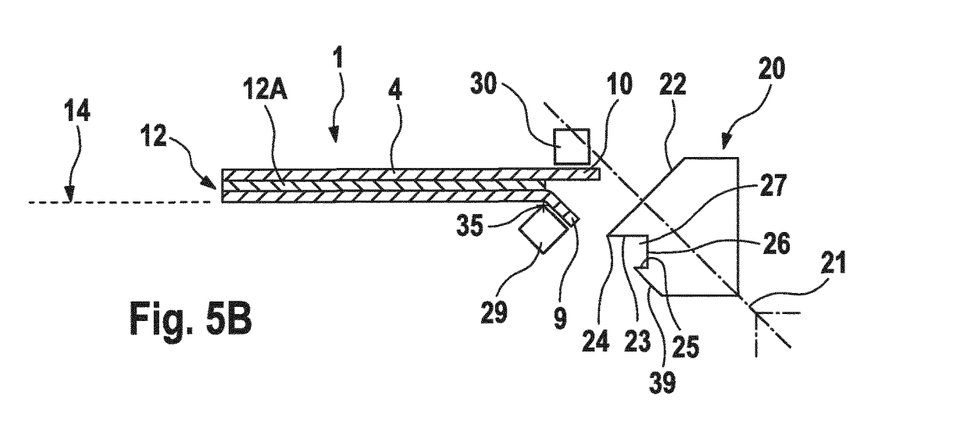
FIG. 5B shows the step of separating the cover and carrier material with the holding and gripper element.
Figure 5C:
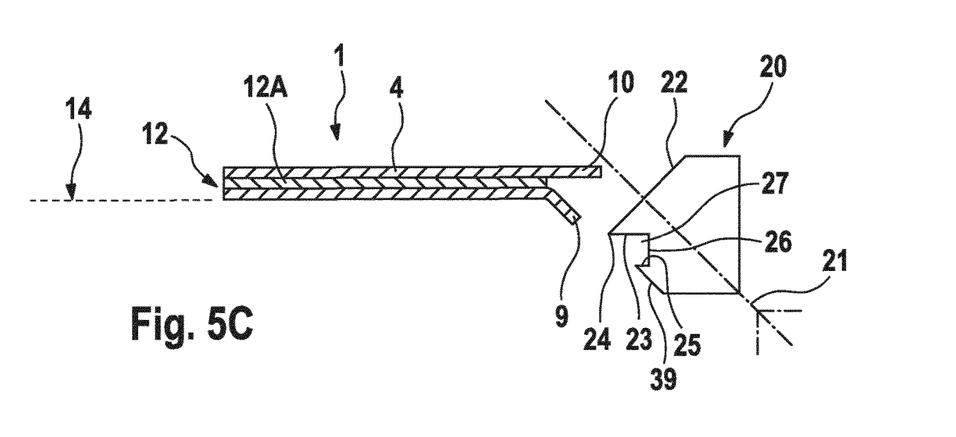
FIG. 5C shows the folding tool in the starting position, in which the holding element is withdrawn and the gripper element is not shown.
Figure 5D:
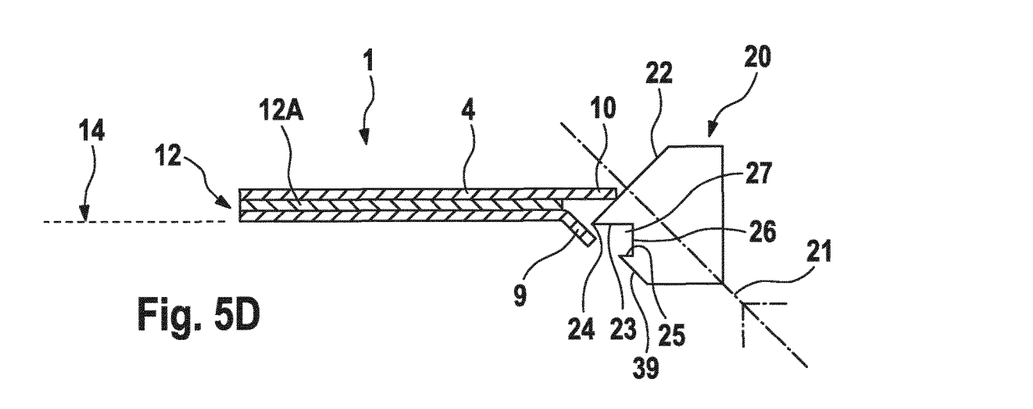
FIG. 5D shows the tool in the position in which the tab is gripped.
Figure 5E:
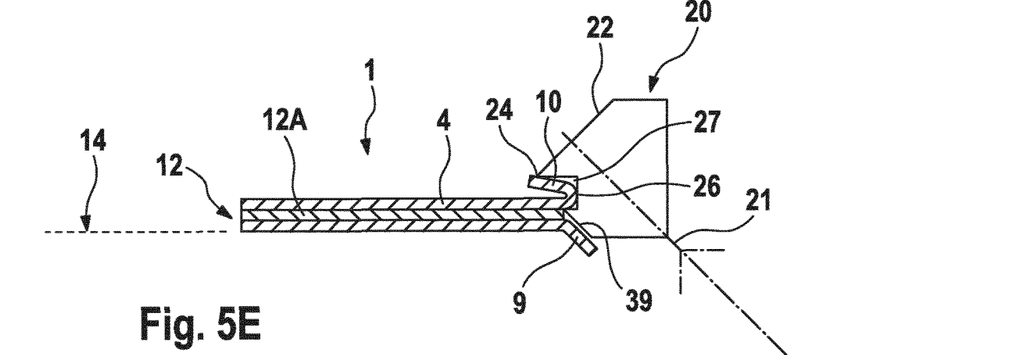
FIG. 5E shows the tool in the position in which the tab is folded over.
Figure 5F:
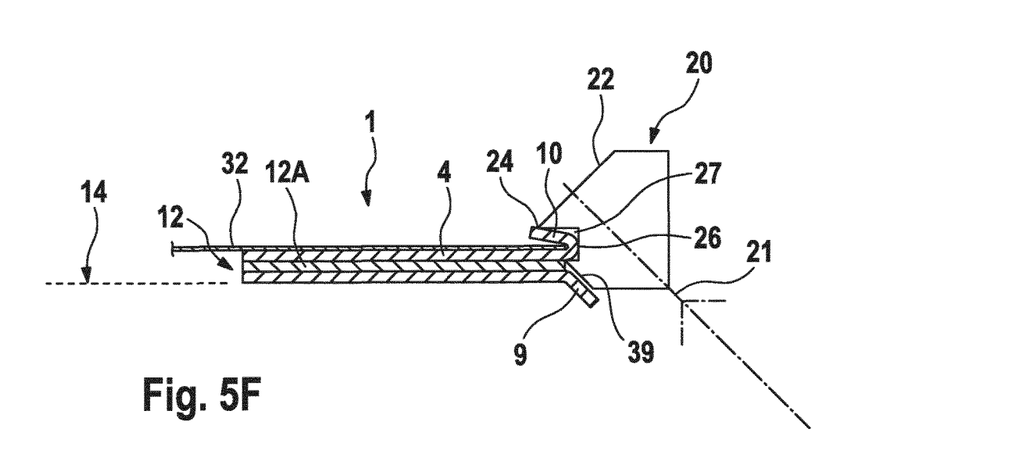
FIG. 5F shows the step of positioning the tab with the positioning element.
Figure 5G:
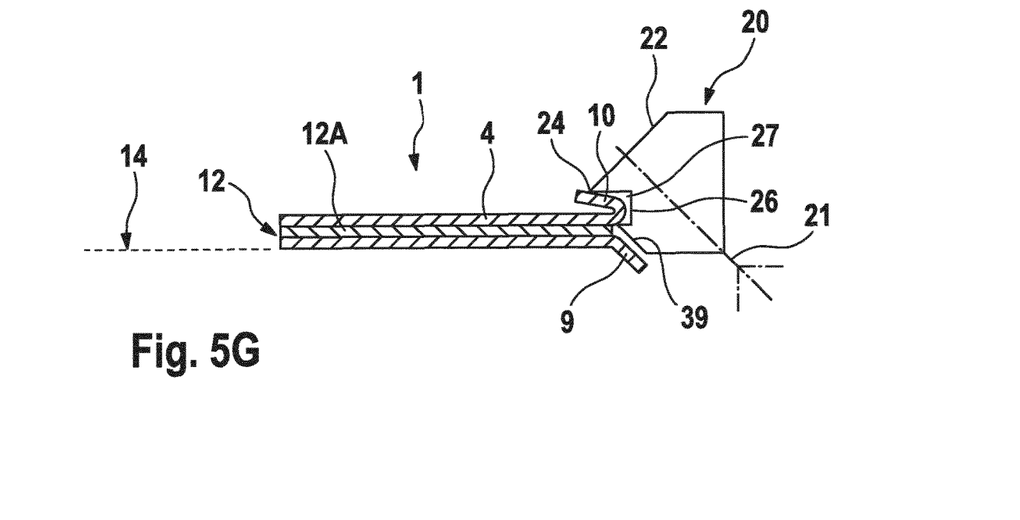
FIG. 5G shows the sensor in the withdrawn position.
Figure 5H:
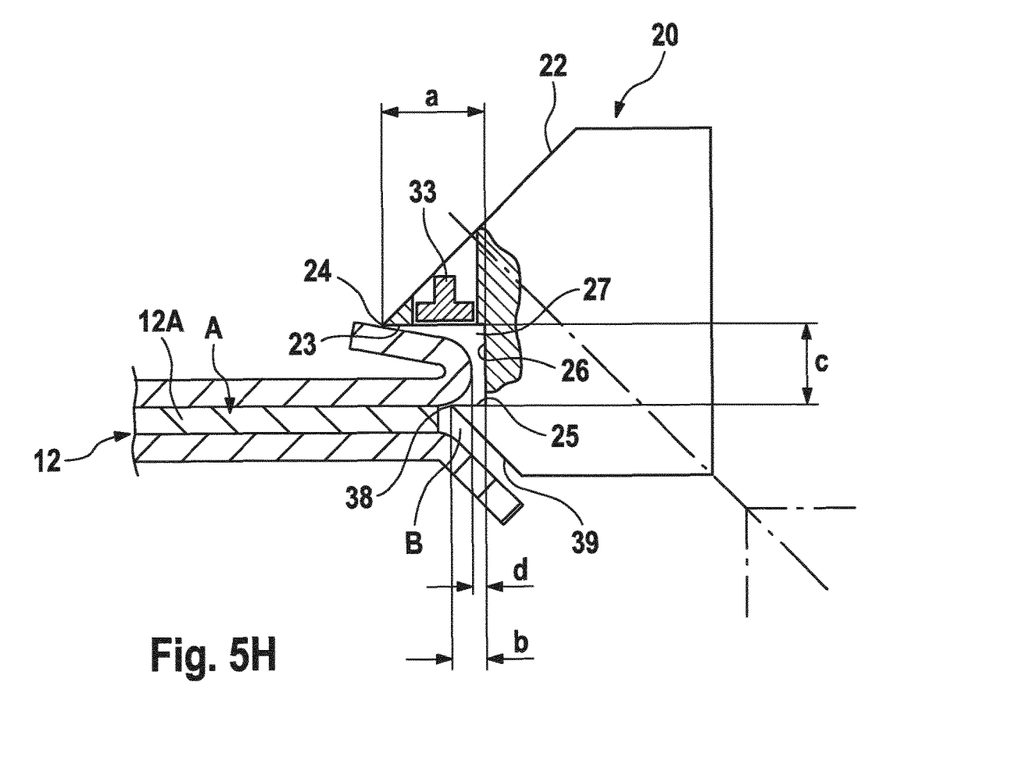
FIG. 5H shows an enlarged view of the tool with the contact-pressure element in a partially sectioned diagram.

The tool 20 has a first contact surface 22, which is orthogonal to the axis 21 on which the tool moves (FIG. 5A, FIG. 5H). In the starting position of the tool 20, the first contact surface 22 faces the removal tab 10. A second contact surface 23, which runs parallel to the sensor surface, is connected to the first contact surface 22. The first and second contact surface surfaces 22, 23 intersect at an edge 24 which faces the removal tab 10 in the starting position of the tool. A third contact surface 25, which runs parallel to the sensor surface, lies opposite and at a distance from the second contact surface 23. The second and third contact surfaces 23, 25 are connected by a fourth contact surface 26, which is perpendicular to the sensor surface. The second and third contact surfaces 23, 25 form the lateral boundaries of a rectangular groove 27 in the tool, in which the fourth contact surface is the base 26 of the groove.

The second contact surface 23 has a length a, which is greater than the length b of the third contact surface 25. The length c of the fourth contact surface 26 is greater than the length b of the third contact surface 25 and less than the length a of the second contact surface 23.

A recoiling angled surface 39, which preferably runs parallel to the axis 21 on which the tool 20 moves, is connected to the fourth contact surface.

In order to separate the section A of the carrier material 12, which is free from the adhesion or adhesive layer 12A, i.e. the connecting tab 9, from the removal tab 10, the device according to the present invention has a device 28 which has a lower gripper element 29 and an upper holding element 30. The gripper element 29 and the holding element 30 are preferably in the form of saucer-shaped suction cups, which are connected to a device (not shown) for producing a vacuum, so that the removal tab and connecting tabs 9, 10 can be held by suction.

In addition, the device according to the present invention has a positioning device 31, which has a positioning element, which can be moved by means of a preferably pneumatic drive device 17 on an axis running parallel to the contact surface 14 in the longitudinal direction X of the device over a short distance, for example, 2 mm, between a retracted position and an extended position (FIG. 5F). The positioning element 32 is a flat tongue, which slides in the longitudinal direction over the surface of the sensor 1 resting on the contact surface 14 (FIG. 5F).

In order to produce the folded edge 8, the device according to the present invention has a longitudinally extended contact-pressure element 33 which extends perpendicular to the longitudinal direction X of the device. The contact-pressure element 33 can be moved in the tool 20 between a raised position and a lowered position on an axis which is orthogonal to the contact surface 14. The contact-pressure element 33, which can be movably guided in the tool, is shown schematically in FIG. 5H.

The gripper element 29 can be swiveled by means of a preferably pneumatic drive unit 34 about an axis 35 which runs perpendicular to the longitudinal direction of the device and parallel to the contact surface 14, in particular, lies in the plane of the contact surface, so that the gripper element 29 moves from a horizontal position, in which the gripper element rests on the underside of the connecting tab 9, into an angled position, in which the connecting tab 9 is folded under and thereby separated from the removal tab 10 (FIGS. 5A and 5B).

The holding element 30 is fixed to the free end of a swivel arm 36 which can be swiveled by means of a preferably pneumatic drive unit 37 about an axis 40 which runs perpendicular to the longitudinal axis X of the device and parallel to the contact surface 14, so that the holding element 30 moves on a circular path between a retracted position and a position in which the holding element rests on the upper side of the removal tab 10.

The individual components of the device according to the present invention are activated by the control unit (not shown) in such a way that the following method steps are carried out.

The holding element 30 and the gripper element 29 are first moved into the position in which the holding element 30 rests on the upper side of the removal tab 10 and the gripper element 29 on the underside of the connecting tab 9 and hold the removal and connecting tab by suction (FIG. 5A). The gripper element 29 is then rotated about the axis 35 so that the connecting tab 9 is separated from the removal tab 10 (FIG. 5B). In order to avoid malfunctions, this process is preferably repeated once, so that the connecting tab is folded over twice. The gripper element 29 now remains in the angled position, while the holding element 30 is retracted into the starting position after switching off the vacuum. The holding element 30 holds the connecting tab 9 in the angled-down position so that the tab cannot be damaged in the following steps.

FIG. 5C shows the folding tool 20 in the starting position, in which the holding element 30 is withdrawn and the gripper element is not shown. The tool 20 is moved from the starting position into the end position (FIG. 5E), in which the edge 24 of the tool 20 moves past the front edge of the foil 11 (FIG. 5D), i.e. impinges upon the sensor 1 from below at the boundary between the section which is free from the adhesion or adhesive layer and the section which is provided with the adhesion or adhesive layer. While the tool 20 is being fed forwards, the removal tab 10 is gripped on the underside by the first contact surface 22 of the tool 20 and folded upwards, in which the removal tab 10 slides along the first contact surface (FIG. 5D). The removal tab 10 now folds over until the tab comes to rest in the groove 27. In doing so, the front edge 38, at which the third contact surface 25 and the angled surface 39 intersect, impinges upon the front edge of the foil, i.e. from below upon the sensor 1 at the boundary between the section of the sensor which is free from the adhesion or adhesive layer and the section of the sensor which is provided with the adhesion or adhesive layer. The connecting tab 10 rests on the angled surface 39 of the tool 20 (FIG. 5E).

The positioning element 32 is then moved from the retracted position into the extended position, so that the positioning element presses the folded-over section of the cover material 4 against the base 26 of the groove (FIG. 5F). The positioning element 32 is then retracted once more.

Hereupon, the holding device 13 is moved back by a predetermined distance d, in which the folded-over section of the cover material 4 is retracted by the distance d, so that the folded-over section is exactly positioned in the groove 27 in order to produce the folded edge 8 (FIG. 5G, FIG. 5H). This distance is very small and corresponds to the so-called clearance of the tool.

The contact-pressure element 33 is now moved from the raised position to the lowered position, so that the contact-pressure element 33 presses onto the folded-over removal tab 10 from above (FIG. 5H) in order to produce a defined folded edge 8 (FIG. 1) The contact-pressure element is then moved back once more into the raised starting position. The tool 20 is then moved back into its starting position, the holding device 13 into the extended position and the holding element 30 into its basic position.

The device according to the present invention can be fed fully automatically by means of a feed device which is not shown.

The invention claimed is:

1. A device for folding a cover material on a medical sensor having a carrier material which, on one side, in a first section, has an adhesion or adhesive layer and, in a second section, has no adhesion or adhesive layer, wherein a cover material, which forms a tab in a third section which overlaps the second section of the carrier material, is applied to the carrier material, the device comprising:

a holding device having a contact surface configured for placement of the medical sensor;

a tool arranged next to the holding device and having a first contact surface and a second contact surface which intersect at an edge which runs parallel to the contact surface of the holding device, wherein the tool is movably guided on an axis which runs at an angle to the plane of the contact surface of the holding device; and a movably guided contact-force element configured to exert pressure to produce a folded edge.

2. The device according to claim 1, wherein the tool has a third contact surface which lies opposite and at a distance from the second contact surface.

3. The device according to claim 2, wherein the second and the third contact surfaces are substantially parallel to one another.

4. The device according to claim 2, wherein the second contact surface extends beyond the third contact surface.

5. The device according to claim 2, wherein the second and the third contact surfaces form lateral boundaries of a groove in the tool.

6. The device according to claim 1, wherein the holding device is movably guided on an axis which runs parallel to the contact surface of the holding device.

7. The device according to claim 6, wherein the axis on which the positioning element is movably guided runs parallel to the axis on which the holding device is movably guided.

8. The device according to claim 1, further comprising:
a holding element, wherein the holding element is configured to hold the tab, wherein the holding element is arranged next to the holding device above the contact surface of the holding device.

9. The device according to claim 8, wherein the holding element is arranged on a swivel arm.

10. The device according to claim 1, wherein the first contact surface runs substantially orthogonally with respect to the axis on which the tool is movably guided.

11. The device according to claim 1, wherein the second contact surface lies in a plane which is substantially parallel to the contact surface of the holding device.

12. The device according to claim 1, wherein the contact-force element is movably guided in the tool on an axis which runs orthogonally with respect to the contact surface of the holding device.

13. The device according to claim 1, further comprising:
a positioning element which is movably guided on an axis which runs parallel to the contact surface of the holding device.

14. The device according to claim 1, wherein the contact surface of the holding device has a contoured depression configured for placement of the second section of the carrier material and the cover material which is applied to the second section, wherein the contoured depression extends as far as the edge of the contact surface of the holding device such that the tab of the sensor which is placed in the depression extends beyond the contact surface of the holding device.

15. The device according to claim 1, further comprising:
a gripper element, wherein the gripper element is configured to separate the second section from the tab, wherein the gripper element is arranged next to the holding device below the contact surface of the holding device, wherein the gripper element is configured to swivel about an axis which runs parallel to the contact surface of the holding device.

16. A method for folding a cover material on a medical sensor having a carrier material which, on one side, in a first section, has an adhesion or adhesive layer and, in a second section, has no adhesion or adhesive layer, wherein a cover material, which forms a tab in a third section which overlaps the second section of the carrier material, is applied to the carrier material, the method comprising:

providing the carrier material and the cover material in a first plane;

providing a tool having a first contact surface facing towards the tab and a second contact surface facing away from the tab on the side of the carrier material and the cover material on which the tab is located, wherein the first and the second contact surfaces of the tool intersect at an edge which runs parallel to the first plane of the carrier material and the cover material and which faces the carrier material and cover material;

moving the tool on an axis which runs at an angle to the first plane of the carrier material and the cover material so that the tab is gripped by the tool and folded over by the tool; and exerting pressure on the folded section of the folded-over cover material to produce a folded edge.

17. The method according to claim 16, wherein the tool has a third contact surface which lies opposite and at a distance from the second contact surface, wherein the folded section is pressed against the third contact surface.

18. The method according to claim 17, wherein the second and the third contact surfaces form lateral boundaries of a groove in the tool, wherein the folded section is pressed against a base of the groove before the folded section is pressed against the third contact surface.

19. The method according to claim 18, wherein the folded section is pressed against the base of the groove via a positioning element which is pushed forward into the groove in a plane parallel to the first plane.

20. The method according to claim 19, wherein the folded section is retracted by a predetermined distance before the folded section is pressed against the third contact surface.

21. The method according to claim 17, wherein the second and the third contact surfaces run substantially parallel to one another.

22. The method according to claim 17, wherein the second contact surface extends beyond the third contact surface.

23. The method according to claim 16, wherein a gripper element, which grips a side of the carrier material facing away from the cover material, is swiveled about an axis which runs parallel to the plane of the carrier material and the cover material to separate the second section of the carrier material from the tab.

24. The method according to claim 23, wherein during the swiveling of the gripper element, the tab is held on a side facing away from the carrier material by a holding element.

25. The method according to claim 16, wherein the second section is separated from the tab before the tool is moved.

26. The method according to claim 16, wherein the first contact surface runs substantially orthogonally with respect to the axis on which the tool is moved.

27. The method according to claim 16, wherein the second contact surface lies in a plane substantially parallel to the first plane.

28. The method according to claim 16, wherein the carrier material and the cover material are arranged on a fourth contact surface in such a way that the tab extends beyond the fourth contact surface.

* * * * *